United States Patent
Mulye (10) Patent No.: US 7,179,486 B1
(45) Date of Patent: Feb. 20, 2007

(54) PROCESS FOR PREPARING SUSTAINED RELEASE TABLETS

(75) Inventor: Nirmal Mulye, Princeton, NJ (US)

(73) Assignee: Nostrum Pharmaceuticals, Inc., Edison, NJ (US)

( * ) Notice: Subject to any disclaimer, the term of this patent is extended or adjusted under 35 U.S.C. 154(b) by 0 days.

(21) Appl. No.: 09/861,321

(22) Filed: May 18, 2001

Related U.S. Application Data (63) Continuation-in-part of application No. 09/053,592, filed on Apr. 1, 1998, now abandoned.

(60) Provisional application No. 60/042,879, filed on Apr. 1, 1997.

(51) Int. Cl.
*A61K 9/20* (2006.01)
*A61K 9/22* (2006.01)
*A61K 9/26* (2006.01)
*A61K 9/28* (2006.01)

(52) U.S. Cl. .................. 424/465; 424/464; 424/468; 424/470; 424/474

(58) Field of Classification Search ................ 424/464, 424/465, 468, 469, 470, 471, 474, 489, 490
See application file for complete search history.

(56) References Cited

U.S. PATENT DOCUMENTS

| | | | |
|---|---|---|---|
| 3,065,143 A | 11/1962 | Christenson et al. | |
| 3,388,041 A | 6/1968 | Gans et al. | |
| 3,839,319 A | 10/1974 | Greminger, Jr. et al. | |
| 3,852,421 A | 12/1974 | Koyanagi et al. | |
| 3,870,790 A | 3/1975 | Lowey et al. | |
| 4,167,558 A | 9/1979 | Sheth et al. | |
| 4,226,849 A | 10/1980 | Schor | |
| 4,259,314 A | 3/1981 | Lowey | |
| 4,369,172 A | 1/1983 | Schor et al. | |
| 4,389,393 A | 6/1983 | Schor et al. | |
| 4,439,453 A | 3/1984 | Vogel | |
| 4,555,399 A | 11/1985 | Hsiao | |
| 4,687,662 A * | 8/1987 | Schobel | 424/44 |
| 4,690,822 A | 9/1987 | Uemura et al. | |
| 4,695,467 A | 9/1987 | Uemura et al. | |
| 4,704,285 A | 11/1987 | Alderman | |
| 4,734,285 A | 3/1988 | Alderman | |
| 4,748,023 A * | 5/1988 | Tamas et al. | 424/465 |
| 4,752,479 A | 6/1988 | Briggs et al. | |
| 4,775,535 A | 10/1988 | Lowey | |
| 4,795,327 A * | 1/1989 | Gaylord et al. | 424/468 |
| 4,820,522 A | 4/1989 | Radebaugh et al. | |
| 4,832,957 A | 5/1989 | Dempski et al. | |
| 4,855,143 A | 8/1989 | Lowey | |
| 4,871,548 A | 10/1989 | Edgren et al. | |
| 4,900,755 A | 2/1990 | Dempski et al. | |
| 4,933,182 A | 6/1990 | Higashi et al. | |
| 4,938,967 A | 7/1990 | Newton et al. | |
| 4,968,509 A | 11/1990 | Radebaugh et al. | |
| 4,973,469 A | 11/1990 | Mulligan et al. | |
| 4,983,398 A | 1/1991 | Gaylord et al. | |
| 5,004,613 A | 4/1991 | Radebaugh et al. | |
| 5,007,790 A | 4/1991 | Shell | |
| 5,015,479 A | 5/1991 | Mulligan et al. | |

(Continued)

*Primary Examiner*—S. Tran
(74) *Attorney, Agent, or Firm*—Scully, Scott, Murphy & Presser, P.C.

(57) ABSTRACT

The present invention is directed to the process of preparing a sustained release niacin tablet and the product prepared therefrom.

18 Claims, 2 Drawing Sheets

U.S. PATENT DOCUMENTS

| | | |
|---|---|---|
| 5,023,245 A | 6/1991 | Kuhrts |
| 5,073,380 A | 12/1991 | Babu et al. |
| 5,100,675 A | 3/1992 | Cho et al. |
| 5,126,145 A * | 6/1992 | Evenstad et al. ............ 424/465 |
| 5,128,142 A | 7/1992 | Mulligan et al. |
| 5,164,193 A | 11/1992 | Okada et al. |
| 5,190,763 A | 3/1993 | Edgren et al. |
| 5,200,193 A | 4/1993 | Radebaugh et al. |
| 5,202,128 A | 4/1993 | Morella et al. |
| 5,262,171 A | 11/1993 | Login et al. |
| 5,268,181 A * | 12/1993 | O'Neill et al. ............... 424/465 |
| 5,292,534 A | 3/1994 | Valentine et al. |
| 5,370,878 A | 12/1994 | Shah |
| 5,427,799 A | 6/1995 | Valentine et al. |
| 5,445,826 A * | 8/1995 | Kuhrts ........................ 424/451 |
| 5,910,322 A * | 6/1999 | Rivett et al. ................. 424/484 |

* cited by examiner

PROCESS FOR PREPARING SUSTAINED RELEASE TABLETS

RELATED APPLICATIONS

This is a continuation-in-part of application U.S. Ser. No. 09/053,592 filed on Apr. 1, 1998 now abandoned, which in turn is claiming benefit from U.S. Provisional Application having Ser. No. 60/042,879 filed on Apr. 1, 1997.

FIELD OF THE INVENTION

The present invention is directed to a process for preparing sustained release tablets containing directly compressible or granular or granulated niacin, and the formulations prepared by said process.

BACKGROUND OF THE INVENTION

Niacin is an important dietary supplement. For example, niacin plays an important role in metabolism, acting as an hydrogen and electron transfer agent in carbohydrate metabolism. Furthermore, niacin forms part of nicotinamide adenine dinucleotide (NAD) and nicotinamide adenine dinucleotide phosphate (NADP), which are important intercellular carriers of reducing electrons in the electron transport system in living organisms. Moreover, niacin containing coenzymes participate in a variety of biological reactions, e.g., lipid catabolism and oxidative deamination. In fact, niacin deficiency has been identified as the leading cause of a medical malady known as pellagra.

Niacin has also been found to have therapeutic value. It is highly effective in reducing elevated levels of plasma cholesterol and triglycerides, and is thus useful in treating hypercholesterolemia. In addition, niacin exhibits adipose tissue lipolysis, reduces plasma free fatty acid levels and decreases very low density lipoprotein synthesis. In addition, niacin has demonstrated value in preventing manifestations of arteriosclerotic heart disease.

To administer niacin as a diet supplement, the present inventor sought to make tablets containing same since tablets have shown to be one of the best methods for administering pharmaceuticals.

Tablets have several advantages over capsules. For example, for some drugs, it is recommended that the patient begin taking a smaller dose and gradually over time increase the dose to the desired level; this regimen can help avoid undesirable side effects. Tablets are preferable to capsules in this regard because a scored tablet easily can be broken to form a smaller dose.

In addition, tableting processes are generally simpler and less expensive than bead coating and capsule formation. Further, tablets can be safer to use because they may be less subject to tampering.

In common tableting processes, material which is to be tableted is deposited into a cavity and one or more punch members are then advanced into the cavity and brought into intimate contact with the material to be pressed, whereupon a compression force is applied. The material is thus forced into conformity with the shape of the punches and the cavity.

Three basic compression steps are common to most tableting operations, i.e., direct dry compression, wet granulation and dry granulation.

Direct compression was historically used to describe compression of a single crystalline compound into a compact tablet form without the use of additional ingredients. However, direct compression techniques are encumbered by a number of problems; few compounds possess the necessary properties to make such compaction possible. In addition, in direct compression, the flow properties of particle-sized powders are inadequate to ensure even filling of the die cavities of tablet presses. Furthermore, entrapment can occur, which interferes with the formation of the tablet.

Where direct compression is not possible, granulation has been used as a pretreatment. This technique is most frequently used. Materials to be delivered are pretreated to form granules that readily lend themselves to tableting. As commonly defined, "granulation" is any process of size enlargement whereby small particles are gathered together into larger permanent aggregates to yield a free flowing composition having a consistency similar to that of dry sand. This may be accomplished by agitation in mixing equipment or by compaction, extrusion or globulation. In granulation, the active or intended ingredients are generally admixed with a compression vehicle. The compression vehicle or filler must have good compressibility, good flowability and stability under normal ambient conditions as well as being low in cost and satisfactory in both texture and appearance. In addition to compression vehicles, tablet formulations typically include other additives such as diluents, flavor, colors, disintegrating agents and lubricants, all of which may be added during granulation or thereafter.

Although the wet granulation and the dry granulation methods are the most commonly used, each of these techniques requires several steps in order to prepare the drug. For example, the wet granulation process typically includes mixing the components, usually in powder form, preparing the granulating binder solution, thoroughly mixing the components with the granulating binder solution to form a dough, coarse screening the mess through a sleeve, drying, grinding, adding a lubricant and compressing the tablets from the resulting mixture. Dry granulation involves the steps of mixing the powder components, compressing the mixture into hard slugs, grinding the slugs into desired particle size, screening, adding fillers, if necessary, and compressing the mixture into tablets.

These are the general steps normally used to make conventional immediate release dosage forms. However, modifications have been made to prepare sustained release formulations.

Sustained release formulation for drugs are prepared in such a manner as to effect sustained or slow release into the gastro-intestinal digestive tract of humans or animals over an extended period of time. They have several advantages over conventional immediate release dosage forms. For example, there is less frequent administration of the active ingredient and more frequent resultant patient regime compliance, thereby avoiding the problems inherent in ensuring timely consumption thereof by the patient. Moreover, sustained release formulations achieve a small sustained blood level response to active ingredient in the formulation relative to conventional immediate release drug forms. It also reduces or possibly eliminates toxic or side effects which are caused by frequent administration of active ingredients through the peaks and valleys of blood levels caused by multiple ingestion thereof. By providing a slow and steady release of the active ingredient over time, absorbed concentration spikes are mitigated or eliminated by effecting a smoother and more sustained blood level response.

Sustained release therapeutic dosage forms are based on many and varied principles. For example, one of the techniques of these preparations involves formation of the drug in generally spherical pellet forms wherein a specific quantity of pellets are set aside for immediate release and the remaining dry pellets or spheres are coated with various thicknesses of a suitable fat or fatty resinous like coating. When fractions of the pellet are blended together and then filled into capsules or pressed into tablets without destroying the integrity of the coating, suitable slow or sustained release forms may be effected. Another technique is to admix the therapeutic agent with fats and solid polyhydric alcohols, such as polyoxyethylene glycol distearate, and press the mixture into tablets to form an erosion matrix to effect slow or sustained release dosage forms. Another method employs the use of a therapeutic agent bound to an ion exchange resin or otherwise complexed with an organic or inorganic molecule and embedded in a waxy core or granule and administered in capsule or pressed tablet form. Still another method employs the use of an indigestible film former such as methyl cellulose applied to a powder or granule base containing a therapeutic agent followed by subsequent forming into compressed tablets to effect slow or sustained release. Yet, another method employs a tablet containing a specific drug coated with an indigestible film in which the film is pierced by a layer beam to allow for a small and precise portal from which the drug is slowly released.

Although these are just a few examples of some of the techniques utilized to prepare sustained release formulations, the point is clear. These techniques require several steps, utilizing sophisticated procedures. The present inventor sought a much simpler procedure which is more efficient and only requires a few steps.

Recently, less complicated procedures have been utilized to prepare sustained release formulations as described hereinbelow.

U.S. Pat. No. 5,292,534 discloses a sustained release composition for various active ingredients, including niacin, in mixture with Xanthum gum and lubricant.

Gaylord, et al. in U.S. Pat. No. 4,795,327 disclose a method for the preparation of a therapeutically active solid unit dosage form having a controlled and prolonged release pattern upon administration consisting of compressing and shaping a mixture of a therapeutically active medicament and a carrier based material consisting of a mixture of one or more water-soluble nonionic cellulose ethers and an anionic surfactant, and wherein at least one of the cellulose ethers is methyl cellulose or hydroxypropylmethylcellulose having a number average molecular weight of at least 50,000. It discloses that the anionic surfactant was necessary, for in its absence, the tablet exhibited a very poor release profile.

U.S. Pat. No. 4,983,398 to Gaylord, et al. discloses another method for the preparation of a therapeutically active unit dosage form having a controlled and sustained release pattern upon administration comprising mixing, shaping and compressing a therapeutically active medicament and a carrier base material consisting essentially of (a) an alkali metal carboxylate and (b) one or more water-soluble nonionic cellulose ethers, at least one of which is hydroxypropylmethylcellulose having a number average molecular weight of at least 50,000. They show that the presence of the alkali metal carboxylate is necessary to retard the release rate of the drugs.

U.S. Pat. No. 4,775,535 to Lowey, disclose a method of preparing controlled release pharmaceutical tablets, by adding a cellulose ether base material, e.g., hydroxypropylmethylcellulose, and an active therapeutic agent to form a mixture, thoroughly and uniformly mixing that mixture, discontinuing the mixing and permitting the uniform mixture to stand for a period of time, typically two to 24 hours or longer, sufficient to cause the therapeutic agent to become bonded to the carrier base material and compressing the mixture to form the solid unit dose tablets.

U.S. Pat. No. 4,734,285 describes a process for providing sustained release solid tablets of a therapeutically active composition comprising:

(a) comminuting a water-soluble hydroxy-propyl methylcellulose ether having a hydroxy propoxy substitution of from about 7 to about 12 weight percent, a methoxy substitution of from about 28 to about 30 weight percent, and a number average molecular weight of at least 50,000 to a relatively fine particle sized cellulose ether composition, having 2% aqueous solution viscosity of at least 800 cps and at least 90% by weight of the cellulose ether particles pass through a 100 mesh screen, and (b) intimately mixing the active composition in the form of a powder with a functionally effective amount of fine particle sized cellulose ether composition and (c) subjecting the mixture of active composition and fine particle sized cellulose ether composition to compression conditions to form a solid tablet.

U.S. Pat. No. 5,268,181 discloses the preparation of niacin tablets containing hydroxypropylmethylcellulose, hydrogenated vegetable oil, and silicon dioxide utilizing the wet granulation processes. For example, 16 liters of water were heated in 95° C. in a stainless steel container and hydroxypropylmethylcellulose was mixed therewith until a homogenous suspension was obtained. 48 liters of water was added until a clear solution was obtained. Then hydrogenated vegetable oil, which was sized through a No 1 mesh screen and coloring was added thereto. Niacin powder was added thereto and 22 additional Methocel®E15LV (hydroxypropylmethylcellulose) was sprayed on and mixed and the resulting wet granulation was sized through a USS No 16 screen, and dried. It also discloses the formulation of the niacin tablets using a fluid bed process, which process is similar to the one described herein above except it was prepared in a fluid bed container.

U.S. Pat. No. 5,023,245 discloses the preparation of niacin formulations in which the niacin is in combination with a gel-forming dietary fiber, such as guar gum. It discloses the preparation of a niacin tablet by granulating the niacin in a fluid bed granulator by spraying the niacin powder with NaCMS and ethyl cellulose to form granulated niacin (95%). 160 mg of the niacin was then mixed with psyllium husk powder (600 mg) or other gel forming dietary fiber, calcium carbonate (100 mg), citric acid (25 mg) and microcrystalline cellulose (25 mg).

However, even many of these processes described hereinabove were quite complex. Many of these formulations required components, which, in a simpler process, could be eliminated. The inventor sought to prepare a formulation which was simpler and did not require as many components. In addition, in many of the processes described hereinabove, the processes required several steps, which affected the cost and efficiency of the process. The inventor sought a process which is much simpler than those and which provided an excellent release profile.

However, there are many factors which must be considered in making a sustained release formulation, some of which are general and some of which are specific to the active ingredient. For example, the sustained release formulation must have an excellent drug release profile, and yet, it must be stable and have a long shelf life. Furthermore, it is of considerable importance in the administration of controlled long acting release tablets that the rate of release of the active agent from the tablet be consistent and uniform among tablets prepared at different times and in different manufacturing batches. It is critical both from the standpoint of safety as well as the reliability thereof that the bioavailability characteristics of the tablet prepared be substantially uniform and comparable. In the absence of such reliability, the dangers to a patient are significant, especially if active ingredients are released at faster or slower rate than are assumed. Moreover, niacin itself presents a problem. The classic concept of a sustained release dosage regime is to release 20–35% of the therapeutic agent within the first hour and to sustain the remaining portion of the therapeutic agent over a 8–12 hour period. This is problematic especially since the niacin therapeutic dose is 500–1000 mg and especially since niacin causes a flushing response in most subjects with a dosage release of more than 75 mg within a one hour period. In addition, niacin in concentrations greater than 50% by weight has been found difficult to compress into a tablet using direct compression methods. Further, niacin in powder form shows very poor compressibility and flow properties. But to make tablets of niacin, it is essential that the medicament is compressible and exhibits good flow properties.

However, the present inventor has found a means of overcoming these difficulties and has found a process for producing a sustained release oral dosage form of niacin that is prepared in relatively few steps and which is stable, has a long shelf life and exhibits an excellent drug release profile. Moreover, the drug release profile of the sustained release formulation is uniform and consistent among tablets prepared in a given manufacturing batch and among tablets prepared at different times and in different manufacturing batches.

SUMMARY OF THE INVENTION

Accordingly, the present invention is directed to a process of preparing a sustained release oral dosage form of niacin comprising granulated or compressible niacin, a lubricant, a polymeric sustained release material, and optionally a filler, said process comprises:

(a) blending from about 65% to about 98% by weight of said niacin in granulated or granular form with a lubricating effective amount of a lubricant and about 1 to about 25% of a polymeric sustained release material and 0 to about 25% filler until the mixture is homogeneous with respect to the niacin and (b) compressing the product of (a) into a tablet.

In another variation, the process comprises (a) blending from about 65% to about 98% by weight of said niacin in granulated or granular form with about 1 to about 25% of a polymeric sustained release material and 0 to about 25% filler until the mixture is homogenous with respect to the niacin;

(b) adding a lubricating effective amount of a lubricant to the mixture of (a) and mixing the resulting mixture until the lubricant is substantially evenly dispersed in said mixture and (c) compressing the product of (a) into a tablet.

The present invention is also directed to the formulation produced by said process.

DETAILED DESCRIPTION OF THE INVENTION

It has now been discovered that unit dosage formulations, especially tablets, comprising the ingredients described hereinabove and formulated in the manner indicated produce a prolonged action and advantageous delivery system. More specifically, as a result of the methodology used to make the present formulation, a product is obtained which has the desired hardness, low level of friability and an excellent and regular delayed release pattern. Furthermore, the tablets are prepared in a relatively simple and economical manner.

The percent of the ingredients required in the formulation of the present invention, the niacin, the polymer, filler and lubricant, and other ingredients, are calculated on a dry weight basis without reference to any water or other components present. Thus, these four components together constitute 100 percent of the formulation for purposes of calculating individual percentages. If additional ingredients are present in the formulation, then the actual percentages for these four ingredients will change accordingly, but their relative concentration to each other will remain the same. If other ingredients are present, the sum of all of the components constitutes 100 percent of the formulation for purposes of calculating individual percentages.

The term "unit dosage form", as employed herein refers to physically discrete units suitable as unitary dosages to human subjects and other mammals, each unit containing a predetermined quantity of active material calculated to produce the desired effect, in association with the other ingredients of the formulation disclosed herein.

The term "direct compression" and terms of like language, as used herein, mean that the composition can be formed into a tablet using well known tableting apparatus and processes without need for the addition of any additional material to the composition. As used herein, the term "kp" means kilopounds, a well known unit of force for expressing hardness or crushing strength of pharmaceutical tablets when such hardness is determined.

In preparing a sustained release formulation, in general, several factors must be taken into consideration. Obviously, the formulation will vary depending upon the identity of the active ingredient. In addition, the interaction of the active ingredient, in this case, niacin, with the other components must also be taken into account. In addition, a key element is the type and amount of sustained released polymers as well as the process for preparing same.

One of the critical elements in preparing sustained release tablets of the present invention is the presence of the granulated or granular niacin. The inventor has found that the granulated niacin facilities the formation of and the necessary interaction in the tablet with the other ingredients.

Surprisingly, the powdered form does not form a satisfactory tablet exhibiting the desired characteristics. Without wishing to be bound, it is believed that the powder cannot be formulated into a satisfactory tablet because it lacks fluidity and compressibility. Good flow properties are essential for the transport of the material through the hopper, into and through the feed frame and into the dies. Powders are not in the physical form that flows smoothly and uniformly, i.e., it is not spherical or spherical-like in shape. It is the sphere shape that is the ideal physical form since these offer minimum contact surfaces between themselves and with the walls of the machine parts. In addition, the powder has poor compressibility, i.e., the property of forming a stable compact mass when pressure is applied. Powder particles are believed to have poor cohesion with other powder particles, and thus are unable to form aggregates capable of compaction.

On the other hand, it is believed that the granulation process improves the fluidity and compressibility. Through the granulation process, it is believed, without wishing to be bound, that the particles become substantially regularly shaped aggregates, and preferably sphere-like, i.e., they become granular, thereby enhancing its fluidity. In addition, it is believed that the granulation process imparts to the particle the ability to aggregate with other particles, thereby forming a cohesive aggregate capable of compaction. It is preferred that as a result of granulation, the average size of the particles of the niacin is greater than about 10 microns, and more preferably greater than about 20 microns, and most preferably greater than about 50 microns but not more than about 500 microns, and most preferably form about 100 microns to about 500 microns.

Niacin is commercially available as powdered form and in granulated form. Preferably, the diet supplement, i.e., niacin, is substantially anhydrous. If the niacin is not in the dry compressible or granulated form, it can be made into the dry granulated form, by techniques known to the skilled artisan.

Compression granulation involves compacting the niacin or formulation containing the niacin by means of a tablet press or specially designed machinery followed by milling and screening. One methodology of granulation is "slugging" wherein the niacin or formulation containing the niacin is compressed on heavy duty tablet presses. Generally, the pressure is greater than in regular compression and the resulting tablets or slugs are very large (e.g., 2.5–5.0 cm in diameter) and weigh 20–30 grams, which are then ground and screened to appropriate mesh size. Another common methodology is chilsonation, which involves dry compaction of the diet supplement using roller compactors. Roller compactors utilize two rollers that revolve towards each other. By means of a hydraulic ram forcing one of the rollers against the other, the machine exerts pressure on the material flowing between the rollers. The material is fed between the rollers by a screw conveyor system. The compacted mass is then screened or milled.

Another surprising aspect of the present invention is that only the niacin is required to be granulated. The present process does not require the other ingredients to also be in granular form, however, as indicated hereinbelow, it is preferred that the filler, if present, especially dicalcium phosphate, be in granular or granulated form. Thus, it is not necessary to granulate the other materials added to the formulation, and in fact, it is preferred that the other ingredients in the formulation not be granulated, with the exception noted above.

It should also be noted that a blend containing high levels of hydrophilic polymers such as hydroxypropylmethyl cellulose (HPMC) are difficult to granulate using aqueous solvents. Alternatively, people have used pharmaceutical binders such as polyvinylpyrrolidine (PVP) and a non-aqueous granulating solvent such as isopropyl alcohol (IPA). The invention described here overcomes that difficulty by only granulating the drug and mixing the hydrophilic polymers afterwards.

The niacin is present in the sustained release formulation of the present invention in amounts ranging from about 50% and more preferably from about 65% by weight to about 98% by weight of the tablet. In a preferred embodiment, the niacin is present in amounts ranging from about 70% by weight to about 95% by weight.

Niacin is preferably present in a granular form. The granular form can be achieved by increasing the particle size of niacin using methods known in the art. The methods include, but are not limited to, dry granulation where niacin powder is compacted and then milled to the required size, crystallization where the niacin is produced with a greater particle size, and the like. The required average particle size must be greater than about 10 microns, preferably greater than about 20 microns, more preferably greater than about 50 microns, the most preferred range of average particle size being about 100 to about 500 microns. Additional ingredients such as diluents or binders can be added to improve the process of increasing the particle size of niacin. Such additions are considered within the scope of this invention.

Another important aspect of the present formulation is the polymeric sustained release material. The objective in preparing a sustained release tablet is to minimize the size of the tablets. Thus, the identity of the sustained release formulation became critical. In an embodiment of the present invention, it is preferred that the sustained release material is one that swells, i.e., becomes viscous when in contact with water, but does not require much material to achieve this; obviously the more sustained release added, the larger will be the tablet. Finally, the sustained release material must maintain the mechanical integrity, that is cohesiveability with the tablet in an aqueous environment.

Polymeric release materials especially various forms of hydroxypropylmethyl cellulose have been utilized as sustained release material, and the inventor has found that specific sustained release polymers are effective in achieving the characteristics he designed. The sustained release polymers which are most effective in the niacin formulation of the present invention are cellulose derivatives, such as cellulose acetate, hydroxypropylmethylcellulose (HPMC), hydroxypropylcellulose (HPC), hydroxyethylcellulose (HEC), sodium carboxymethylcellulose (NaCMC), and the like, polyvinylpyrrolidone (PVP), polyethylethylene oxide, ethyl cellulose, methyl methacrylate copolymers, e.g., a copolymer of methyl methacrylate and lower alkyl esters of acrylic acid (e.g., copolymers of methyl methacrylate and ethyl acrylate and combinations thereof) and combinations thereof. By "lower alkyl", it is meant an alkyl group having 1–6 carbon atoms, which may be branched or straight-chained, such as methyl, ethyl, propyl, isopropyl, butyl, isobutyl, n-butyl, sec-butyl, pentyl, isopentyl, hexyl and the like. In order to accommodate a sufficient amount of a high dosage niacin in a solid unit dosage form, without significantly increasing the size of the latter, the polymeric materials are effective at relatively low concentrations in retarding the release of the niacin. The preferred polymeric material is hydroxypropylmethylcellulose and a copolymer of methyl methacrylate and ethyl acrylate. The preferred hydroxypropylmethyl cellulose has a molecular weight greater than 50,000, a methoxy content of about 16–24% by weight and a hydroxypropoxyl content of 4–32 weight %. Especially preferred are Methocel 90HG 4000 cps and Methocel 90 HG 15,000 cps, now known as Methocel K4M and Methocel K15M, respectively, which have a 19–24 weight % methoxyl content and a 4–12 weight % hydroxypropoxy content. The 4000 cps and 15,000 cps viscosities indicate that the polymers have number average molecular weights of 89,000 and 124,000, respectively. One variety of hydroxypropyl method cellulose can be used alone or in combination with other sustained release polymeric material. It is preferred that if a hydroxypropyl methyl cellulose is used alone, that it has a viscosity of at least 3,000 cps and more preferably greater than or equal to 4,000 cps and most preferably greater than or equal to 8,000 cps.

The inventor has found that in the present formulation the amount of sustained release polymeric material is critical to the present invention. If too much is utilized, then too little niacin is released, while if too little is present, then the niacin is released too quickly. However, the inventor has found that an excellent drug profile release is achieved if the sustained release polymeric material is present in amounts ranging from about 1% to about 25% by weight of the tablet, and more preferably from about 5% to about 18% by weight, more preferably in amounts greater then about 10% (w/w) and most preferably from about 15% to about 20% by weight.

The present inventor has found that if the proper particle size of niacin is used, as defined by the present invention it is not necessary to add a hydrophobic component to aid the wet granulation procedure. Moreover, if the proper particle size of niacin is used, as defined by the present invention, an additional binder is also not necessary, but nevertheless a binder and/or a hydrophobic component may be added as optional ingredients. The preferred mode for preparing the tablet when a water soluble polymer as the sustained release polymer is used is dry granulation, i.e., compressing a dry blend of the components, i.e., niacin in granulated or compressible forms lubricant, and polymeric sustained release material, and optionally other adjuvants, such as filler, and the like. Wet granulation procedure using a solvent may be used if a water insoluble sustained release polymer, such as methylmethacrylate, is utilized. Even when wet granulation procedure is used, no hydrophobic component or an additional pharmaceutical binder is required although these may be added as optional ingredients.

In addition, the sum of the niacin plus polymeric release material ranges from about 90% to about 98% by weight of the tablet.

The other essential ingredient of the present invention is the lubricant. "Lubricant", as used herein, refers to a material which can reduce the friction between the die walls and the punch faces which occurs during the compression and ejection of a tablet. The lubricant prevents sticking of the tablet material to the punch faces and the die walls. As used herein, the term "lubricant" includes anti-adherents.

Tablet sticking during formation and/or ejection may pose serious production problems such as reduced efficiency, irregularly formed tablets and non-uniform distribution of the niacin in the formulation. To avoid this problem, the present invention contemplates utilizing a lubricating effective amount of the lubricant. Preferably, the lubricant is present in amounts ranging from about 0.1% to about 5% by weight and more preferably from about 1% to about 4% by weight of the tablet. Examples of lubricants include stearate salts, e.g., alkaline earth and transition metal salts, such as calcium, magnesium and zinc, stearic acid, polyethylene oxide, talc, hydrogenated vegetable oil and vegetable oil derivatives, and the like. In addition, the tablet may contain a combination of more than one type of lubricant. Other lubricants that also can be used include silica, silicones, high molecular weight polyalkylene glycol, e.g., high molecular weight polyethylene glycol, monoesters of propylene glycol, saturated fatty acid containing about 8–22 carbon atoms and preferably 16–20 carbon atoms. The preferred lubricants are the stearate salts, especially magnesium and calcium stearate and stearic acid.

The present formulation also contains optional ingredients. One of the optional ingredients is a filler. The filler may be water soluble or water insoluble. A filler is used if needed or desired, although not necessary. However, it is preferred that a filler is utilized. The preferred fillers used in the present invention are those typically used in the pharmaceutical arts for oral tablets; examples include maltodextrin, starch, microcrystalline cellulose, calcium salts, such as calcium sulfate, dicalcium phosphate, tricalcium phosphate, calcium lactate, calcium gluconate, and the like; glycerol phosphate; citrates; and mixtures thereof and the like. The filler, if present, is present in amounts ranging from about 0% to about 25% by weight and more preferably, if present, in amounts ranging from about 1% to about 20% by weight. Since niacin supplies much volume to the tablets, the filler, if present in niacin tablets, is present in amounts less than about 10% and more preferably about 2% to about 8% (w/w).

Other optional ingredients, that are also typically used in pharmaceuticals, may also be present, such as coloring agents, preservatives (e.g., methyl parabens), artificial sweeteners, flavorants, oxidizing agents, and the like. Artificial sweeteners, include, but are not limited to saccharin sodium, aspartame, dipotassium glycyrrhizinate, stevia, thaumatin and the like. Flavorants include, but are not limited to lemon, lime, orange and menthol. The colorants include, but are not limited to various food colors, e.g., FD&C colors, such as FD&C Yellow No. 6, FD&C Red No. 2, FD&C Blue No. 2, food lakes and the like. Examples of anti-oxidants include, ascorbic acid, sodium metabisulphite and the like. These optional ingredients, if present, preferably are present in amounts ranging from about 0.1% to about 5% by weight of the tablet and most preferably less than about 3% (w/w) of the tablet.

The niacin formulations of the present invention are preferably uncoated, but may be coated if desired with one of the many readily available coating systems. Coating the tablets serves to mask the taste of the niacin formulation, make the tablet easier to swallow and, in some cases, improve the appearance of the dosage form. The tablets can be sugar coated according to the procedures well known in the art or can be coated with any one of numerous polymeric film coating agents frequently employed by formulation chemists. Representative examples of such film coating agents include hydroxypropyl methylcellulose, carboxymethylcellulose, hydroxypropylcellulose, methyl cellulose, ethyl cellulose, acrylic resins, providone, polyvinyl diethylaminoacetate, cellulose acetate phthalate, polyvinyl acetate phthalate, acrylic latex emulsions, ethyl cellulose latex emulsions, and the like. If the coating material is present, it is present in less than about 2% by weight of the tablet.

The base of the tablet excludes alkali metal carboxylates such as alkali metal salts of $C_8$ to $C_{40}$, and anionic surfactants, such as alkali metal sulfates of linear and branded alcohols, ethoxylated alcohols, ethoxylated alkylphenols, ethoxylated amides, oils, fatty esters, etc; alkali metal salts of sulfonates of naphthalene, alkylnaphthalene, naphthalene condensates, alkyl substituted benzenes, diphenyl derivatives, α-olefins, petroleum oils, fatty acids as well as the alkali metal salts of dialkyl sulfosuccinates. In a preferred embodiment, the formulation of the present invention excludes alkali metal carboxylic and anionic surfactants especially since the latter would change the properties of the blend and interfere with the tableting abilities of the present formulation.

It is preferred that the tablet of the present invention contains the dry granulated or granular niacin, the lubricant, the sustained release polymer, in combination with a filler.

The formulation of the present invention is prepared by blending the granulated niacin formulation, i.e., niacin with the lubricant, sustained release polymeric material and the other optional ingredients except for the coating material. The ingredients are mixed in a typical blender that is normally utilized in the pharmaceutical arts, such as a Hobart mixer, V-blender, a planetary mixer, Twin shell blender and the like. The ingredients are blended together typically at about ambient temperature; no additional heating is necessary, although slight modifications of temperature therefrom could be utilized. It is preferred that the blending be conducted at temperatures ranging from about 10° C. to about 45° C.

The ingredients in the formulation are preferably mixed together in a large batch, and are intimately intermixed together until the mixture is homogenous with respect to the drug. By homogeneous it is not meant that the mixture itself is homogenous, since the mixture is particulate; but rather it is meant that a sample of the blend equivalent to one unit dosage form contains between about 90% to 110% of the desired amount of the niacin to be utilized. In addition, it is meant that the concentration of the niacin and the other ingredients are substantially uniform throughout the invention, i.e., a substantially homogeneous blend is formed. There is no tempering time required, i.e., it is not necessary to stop the mixing step and permit the ingredients to stand without mixing action and wait for an equilibrium to be established between the components. The proper level of concentration of the components will be achieved during the mixing step.

The preferred mixer is a V-blender, which is commercially available. Preferably, the mixing step takes no more than 1 hour and more preferably from about 20 minutes to about 30 minutes.

When the mixture is homogeneous with respect to the drug, a unit dosage form of the mixture is compressed into a tablet form using a tablet machine typically utilized in the pharmaceutical arts. More specifically, the mixture is fed to the die of a tablet press and sufficient pressure is applied to form a solid tablet. Such pressure can vary, and typically ranges from about 1,000 psi to about 6,000 psi and preferably about 2,000 psi force.

In a variation, all of the above steps are repeated, except that the mixing is initially performed in the absence of a lubricant. When the mixture is homogeneous with respect to the drug, then the lubricant is added and the mixing is continued until the lubricant is substantially evenly dispersed in the mixture. Then the mixing is terminated, and the mixture is immediately thereafter compressed into a tablet, as described hereinabove.

In the dry formulation described herein, it is preferred that the niacin is present in granular form in which the required average particle size is greater than about 10 microns, more preferably greater than about 20 microns, even more preferably greater than about 50 microns, and most preferably ranging in size from about 100 to about 500 microns.

Another procedure for preparing the formulation of the present invention is by the wet granulation process in which all of the components except the lubricant are mixed with a sufficient amount of a granulating solvent to form a substantially uniform blend. The granulating vehicle is one that is inert with the components and has a low boiling point, i.e., preferably less than about 120° C. It is preferably a solvent that contains OH groups, such as an alcohol containing 1–4 carbon atoms, e.g., isopropyl alcohol or ethanol or water and the like. An aqueous dispersion can also be utilized, especially if the polymeric sustained release material is a methyl methacrylate copolymer, as described above. In a preferred embodiment, the type of granulating vehicle used is dependent upon the identity of the sustained release polymer. For example, it is preferred that when the sustained release material is a copolymer of methyl methacrylate and ethyl acrylate, the granulating vehicle is an alcohol such as isopropyl alcohol or an aqueous latex dispersion of said copolymer.

In the wet formulation process, the niacin is preferably present in granular form. More specifically, it is preferred that the average particle size of the niacin is greater than about 10 microns, more preferably greater than about 20 microns, even more preferably greater than about 50 microns and most preferably the average particle size ranges from about 50 microns to about 500 microns.

The substantially uniformly blended mixture may optionally be milled, e.g., passed through a screen, sieve, etc. to reduce the size of the particles thereof. The screen or sieve, and the like is preferably less than about 140 mesh, and more preferably less than about 100 mesh, and even more preferably, less than about 40 mesh, and most preferably less than about 20 mesh.

Next, the blend is dried. In this step, the solvent is removed from the blend by physical means known to the skilled artisan, e.g., by evaporation or filtration. The resulting granules are again milled, e.g., passed through a screen or sieve to further reduce the size of the particles to the desired size. Then the lubricant is added, and the granules are mixed to provide a uniform blend, i.e., homogenous with respect to the supplement and then the resulting mixture is compressed to form a tablet. In a preferred variation, the blend can be simultaneously granulated in the granulation vehicle and dried such as using a fluid bed granulation process.

After the tablet is formed, the tablet is coated with materials normally used in pharmaceuticals, if desired. If coated, the coating is prepared by techniques known in the art. As indicated hereinabove, it is preferably uncoated.

As a result of the process described herein, a tablet product is obtained which has the desired hardness and friability typically found for pharmaceutical tablets. The hardness is preferably 5–25 Kp and more preferably 8–20 Kp. In addition, the tablet has an excellent drug release profile. More specifically, it has a predetermined controlled and sustained action and a regular delayed pattern so that the niacin is available over a period of up to 36 hours, depending upon the precise tablet size, the identity of the active ingredient, hardness and the particular carrier composition. For example, in accordance with the process of the present invention, a controlled release niacin formulation can be prepared wherein the release time is 2–4 hours, 8 to 10 hours, 15–18 hours, 20–24 hours, etc. as desired. Furthermore, the release profile of each formulation is substantially uniform. Finally, the tablets prepared in accordance with the present invention are hard and dense, have low friability and provide controlled and sustained release over an extended period. Solid dry forms prepared by the present invention are stable and their release rate does not change to any significant (if any) extent over an extended period of storage.

Unless indicated to the contrary, all percentages are weight percentages relative to the tablet.

The following non-limiting examples further illustrate the present invention.

EXAMPLE 1

Niacin DC Grade (125 Kg), Methocel K4M (6.85 Kg, Methocel K15M (20.65 Kg) were mixed together in a V blender for 20 minutes. Magnesium stearate (2.5 Kg) was added to the mixture and the mixture was mixed in a V blender for an additional 5 minutes. The above blend was compressed using a tablet press to form a tablet containing 310 mg of material, 250 mg Niacin, 13.7 mg Methocel K4M, 41.3 mg Methocel K15M and 50 mg Magnesium stearate.

EXAMPLE 2

Utilizing the procedure of Example 1, Niacin DC Grade (125 Kg), HPMC K15M (27.5 Kg), DCP (7.5 Kg) and Magnesium Stearate (1 Kg) were blended and mixed together and compressed into a tablet. The tablet produced weighed 322 mg and contained 250 mg of Niacin, 55 mg HPMC K15M, 15 mg DCP and 2 mg Magnesium Stearate.

EXAMPLE 3

The procedure of Example 1 was repeated, except Niacin DC Grade (125 Kg), HPMC K4-M (6.85 Kg). HPMC K-15M (20.65 Kg), and stearic acid (3 Kg) were mixed and blended and compressed into a tablet weighing 311 mg and containing 250 mg Niacin, 13.7 mg HPMC K-4M, 41.3 mg HPMC K-15M and 6 mg stearic acid.

EXAMPLE 4

The procedure of Example 1 was repeated except a 500 mg tablet of Niacin was prepared, containing approximately 644 mg of material: 500 mg Niacin, 110 mg HPMC K15M, 30 mg DCP and 4 mg Magnesium Stearate.

Figure 1:
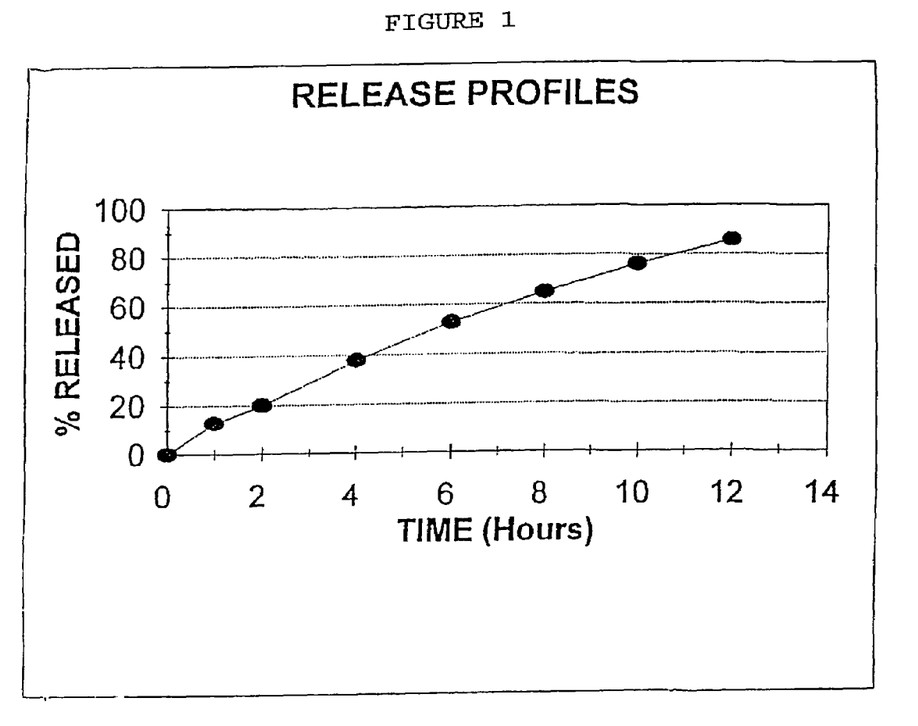
FIG. 1 is a drug release profile of a sustained release 250 mg Niacin tablet placed in deionized water.
Figure 2:
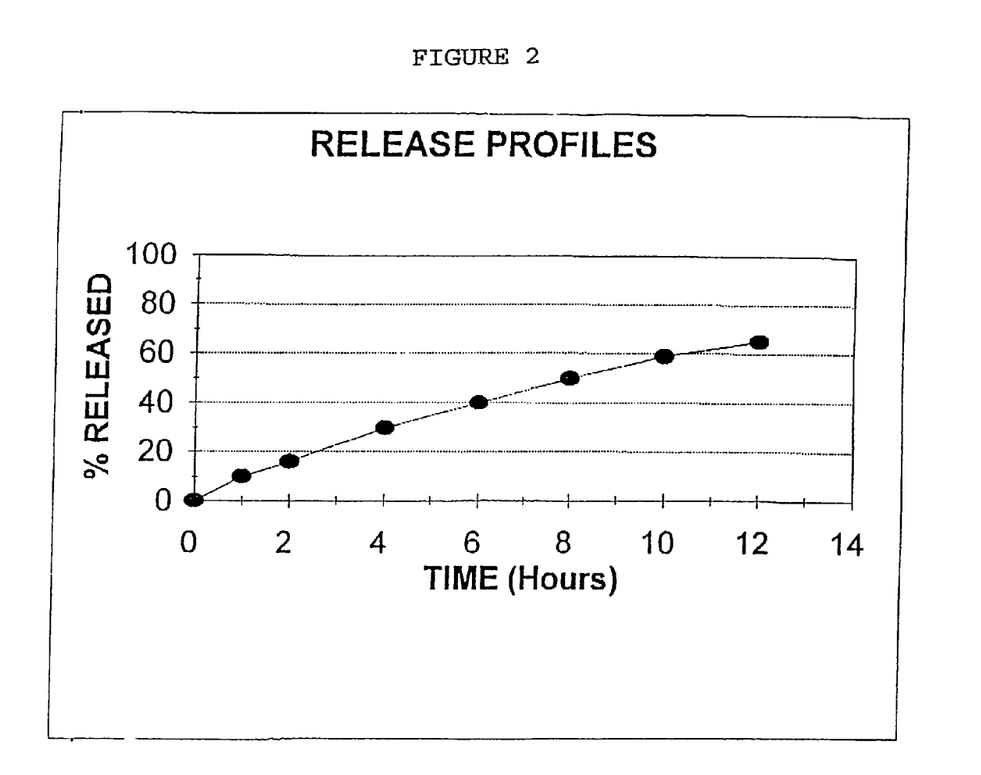
FIG. 2 is a drug release profile of a sustained release 500 mg Niacin tablet placed in deionized water.

The drug profile of the samples of Examples 1, 2 and 4 were tested in accordance with the USP dissolution test as described in the United States Pharmacopoeia utilizing a USP paddle dissolution device at 100 rpm at 37.5° C. in distilled water and buffers at pH 1.2, 4.5 and 7.0. The release profiles are indicated in FIGS. 1 and 2. FIG. 1 is a release profile of the 250 mg Niacin containing tablet prepared in Example 2 while FIG. 2 is a release profile of the 500 mg Niacin Tablet in distilled water prepared in Example 4. The sample of Example 1 had a similar drug profile to that of Example 2.

As clearly shown by the drug profile, the niacin was released slowly but continually over a 12 hour period. In both profiles about 10% was released within the first hour and approximately 20% (w/w) of niacin was released by the end of second hour. The 250 mg niacin tablet released a greater percentage of the niacin at the end of the 12 hour period (~80%) than the 500 mg niacin tablet; however, in all cases, less than 75 mg of niacin was released within any one hour. Thus, the niacin drug release profile showed an excellent release rate of the niacin, and the amount of niacin released was below the threshold level where most people experience side effects, i.e., the flushing response.

EXAMPLE 5

The following formulation was made by a wet granulation technique.

| | Amt. Used (mg) |
|---|---|
| Niacin | 25 |
| Eudragit NE 30D (copolymer of methyl methacrylate and ethyl acrylate) | 40 (as 30% aqueous dispersion) |
| Lactose | 25 |

-continued

| | Amt. Used (mg) |
|---|---|
| Magnesium Stearate | 3 |
| Colloidal Silicon Dioxide | 2 |

All of the ingredients, except the lubricants i.e., Magnesium stearate and the colloidal silicon dioxide and Eudragit NE 30D, were mixed in a planetary mixture until homogenous. The Eudragit NE 30D was added as an aqueous latex dispersion and the components were mixed until a dough was formed. The Dough was pushed through a screening of size 12 mesh and then dried. The resulting granules were milled and then mixed thoroughly with the lubricants and compressed to form a tablet.

The release profile was as follows:

| Time (HRS) | Release (%) |
|---|---|
| 1 | 25 |
| 2 | 34 |
| 4 | 54 |
| 6 | 63 |
| 8 | 75 |
| 10 | 86 |

EXAMPLE 6

The formulation of Example 5 was prepared except 500 mg of Niacin was used. The release profile was as follows:

| Time (HRS) | % Release |
|---|---|
| 1 | 17 |
| 2 | 27 |
| 4 | 44 |
| 6 | 55 |
| 8 | 65 |
| 10 | 74 |
| 12 | 84 |

COMPARATIVE EXAMPLE 1

The procedure of Example 3 was repeated except powder Niacin was utilized instead of the granulated Niacin. A tablet with desirable quality could not be compressed.

The following examples show that the identity of the polymeric sustained release material is critical in preparing the niacin formulation.

COMPARATIVE EXAMPLES 2–7

Utilizing the procedure of Example 1 and the following components, Niacin tablets were prepared:

| | Niacin (mg) | Carbopol (mg) | Lactose (mg) | Magnesium stearate | DCP (mg) |
|---|---|---|---|---|---|
| Comparative Example 2 | 230 | 32 | 33.2 | 1.5% (w/w) | — |

-continued

|  | Niacin (mg) | Carbopol (mg) | Lactose (mg) | Magnesium stearate | DCP (mg) |
|---|---|---|---|---|---|
| Comparative Example 3 | 250 | 16 | 49.2 | 1.5% (w/w) | — |
| Comparative Example 4 | 250 | 9.6 | — | 1.5% (w/w) | 57.2 |
| Comparative Example 5 | 250 | 3 | 62 | 1.5% (w/w) | — |
| Comparative Example 6 | 250 | 6.4 | — | 1.5% (w/w) | 60.4 |
| Comparative Example 7 | 250 | 3 | — | 1.5% (w/w) | — |

A suitable profile for niacin could not be achieved using carbopol in any of the formulations above. In Comparative Examples 2 and 3, the release rate was too slow. In Comparative Examples 4–7, the release rate was much to quick. In addition, in Comparative Example 5, there was a compression problem, i.e., the tablets were laminating after compression (Tablet capping).

COMPARATIVE EXAMPLES 8–9

Utilizing the procedure of Example 1, the following products were prepared:

|  | Niacin (mg) | HPMC* (mg) | Lactose (mg) | Mg stearate |
|---|---|---|---|---|
| Comparative Example 8 | 500 | 50 | 64 | 1.5% (w/w) |
| Comparative Example 9 | 250 | 48 | 17.2 | 1.5% (w/w) |

*a low molecular weight less than 50,000, low viscosity HPMC.

The products of Comparative Examples 8 and 9 had an unsatisfactory release profile, the release was too fast. With respect to Comparative Example 8, 100% was released in 2 hours, while in Comparative Example 9, 40% was released in two hours.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A process for preparing a sustained release tablet comprising granulated or compressible niacin with an average particle size greater than about 20 microns and less than about 500 microns, a lubricant, a sustained release polymer and optionally a filler which process consisting essentially of:
   (a) preparing the granulated niacin by granulating and milling a powdered form of the niacin into granules;
   (b) blending from about 50% to about 98% by weight of substantially dry granulated or direct compressible niacin with a lubricating effective amount of an ungranulated lubricant, about 1 to about 25% (w/w) of an ungranulated polymeric sustained release material selected from the group consisting of cellulose acetate, hydroxypropylmethyl cellulose, hydroxypropyl cellulose, hydroxyethyl cellulose, sodium carboxymethyl cellulose, PVP, ethylene oxide, ethyl cellulose and copolymers of methylmethacrylate and optionally an ungranulated or granulated filler, present in about 0 to about 25% (w/w), until the mixture is homogenous with respect to the niacin; and
   (c) then compressing product of (b) into a tablet.

2. A process for preparing a sustained release tablet comprising granulated or directly compressible niacin with an average particle size greater than about 20 microns and less than about 500 microns, a lubricant, a sustained release polymer and optionally a filler which optionally has been granulated which process consisting essentially of:
   (a) preparing the granulated niacin by granulating and milling a powdered form of the niacin into granules;
   (b) blending from about 50% to about 98% by weight of substantially dry granulated or direct compressible niacin with about 1 to about 25% of an ungranulated polymeric sustained release material selected from the group consisting of cellulose acetate, hydroxypropylmethyl cellulose, hydroxypropyl cellulose, hydroxyethyl cellulose, sodium carboxymethyl cellulose, PVP, polyethylene oxide, ethyl cellulose and copolymers of methylmethacrylate and about 0 to about 25% (w/w) of an ungranulated or granulated filler until the mixture is homogeneous with respect to the niacin and
   (c) adding a lubricating effective amount of an ungranulated lubricant to the mixture of (b), mixing the resulting mixture until the lubricant is substantially evenly dispersed in the mixture and compressing the mixture into a tablet.

3. The process according to claim 1 or claim 2 wherein the lubricant is present in amounts ranging from about 0.1 to 5% by weight.

4. The process according to claim 1 or claim 2 wherein the lubricant is a stearate salt, polyethylene oxide, talc, or hydrogenated vegetable oil.

5. The process according to claim 1 or claim 2 wherein the sustained release polymeric material is a hydroxypropylmethyl cellulose.

6. The process according to claim 5 wherein the hydroxypropylmethyl cellulose has a viscosity greater than about 3,000 cps and a molecular weight greater than 50,000.

7. The process according to claim 1 or claim 2 wherein a filler is present in amounts ranging from about 5 to about 20% by weight.

8. The process according to claim 1 or claim 2 wherein the sum of the niacin and sustained release polymer is present in amounts ranging from about 90% to about 98% by weight.

9. The process according to claim 1 or claim 2 wherein the polymeric material is present in amounts ranging from about 5% to about 18% by weight.

10. The process according to claim 1 or claim 2 wherein the tablet contains about 250, 500 or 750 mg of dry granulated niacin.

11. A process according to claim 1 or 2 wherein niacin is present in amounts greater than about 70% by weight of the tablet.

12. The process according to claim 1 or 2 wherein the polymeric sustained release material is present in amounts ranging from about 10% to about 20% by weight.

13. The process according to claim 1 or 2 wherein the tablet consists essentially of about 65 to about 85% (w/w) niacin, 0.1 to about 5% (w/w) lubricant, about 15% to about 20% of a sustained release polymer, and about 1 to about 8% (w/w) filler.

14. The process according to claim 1 or 2 wherein the average particle size of the niacin is greater than about 50 microns.

15. The process according to claim 1 or 2 wherein the average particle size of the niacin ranges from about 100 microns to about 500 microns.

16. The process according to claim 1 or claim 2 wherein the filler is present in amounts of less than about 10% by weight.

17. A process for preparing a sustained release tablet comprising granulated or compressible niacin with an average particle size greater than about 20 microns and less than about 500 microns, a lubricant, a sustained release polymer and optionally a filler which process consisting essentially of:

(a) preparing the granulated niacin by granulating and milling a powdered form of the niacin into granules;

(b) blending from about 50% to about 98% by weight of substantially dry granulated or direct compressible niacin with a lubricating effective amount of an ungranulated lubricant, about 1 to about 25% (w/w) of an ungranulated polymeric sustained release material selected from the group consisting of cellulose acetate, hydroxypropylmethyl cellulose, hydroxypropyl cellulose, hydroxyethyl cellulose, sodium carboxymethyl cellulose, PVP, ethylene oxide, ethyl cellulose and copolymers of methylmethacrylate and optionally an ungranulated or granulated filler, present in about 0 to about 25% (w/w), until the mixture is homogenous with respect to the niacin;

(c) compressing the product of (b) into a tablet; and (d) then coating the tablet formed in (c).

18. A process for preparing a sustained release tablet comprising granulated or directly compressible niacin with an average particle size greater than about 20 microns and less than about 500 microns, a lubricant, a sustained release polymer and optionally a filler which optionally has been granulated which process consisting essentially of:

(a) preparing the granulated niacin by granulating and milling a powdered form of the niacin into granules;

(b) blending from about 50% to about 98% by weight of substantially dry granulated or direct compressible niacin with about 1 to about 25% (w/w) of an ungranulated polymeric sustained release material selected from the group consisting of cellulose acetate, hydroxypropylmethyl cellulose, hydroxypropyl cellulose, hydroxyethyl cellulose, sodium carboxymethyl cellulose, PVP, ethylene oxide, ethyl cellulose and copolymers of methylmethacrylate and about 0 to about 25% (w/w) of an ungranulated or granulated filler until the mixture is homogenous with respect to the niacin;

(c) adding a lubricating effective amount of an ungranulated lubricant to the mixture of (b), mixing the resulting mixture until the lubricant is substantially evenly dispersed in the mixture and compressing the mixture into a tablet; and (d) then coating the tablet formed in (c).

* * * * *